United States Patent [19]

Hattori et al.

[11] 4,029,640

[45] June 14, 1977

[54] PROCESS FOR PRODUCING AMMONIUM AROMATIC SULFONATE

[75] Inventors: Tatsuo Hattori; Kanzi Katsuragawa; Keiichi Kihara; Isao Ono; Hanzo Tamabayashi, all of Shin-nanyo, Japan

[73] Assignee: Toyo Soda Manufacturing Co., Ltd., Japan

[22] Filed: May 27, 1975

[21] Appl. No.: 580,937

[30] Foreign Application Priority Data

May 27, 1974   Japan ............................. 49-58858

[52] U.S. Cl. .................... 260/79.3 MU; 260/2.2 R; 260/505 N

[51] Int. Cl.² ................ C07C 143/24; C09K 13/06

[58] Field of Search ............. 260/505 N, 79.3 MU, 260/2.2 R

[56] References Cited

UNITED STATES PATENTS

| | | | |
|---|---|---|---|
| 3,579,565 | 5/1971 | Zaslowsky et al. | 260/79.3 MU |
| 3,947,448 | 3/1976 | Subirana | 260/505 N |

*Primary Examiner*—V. P. Hoke
*Attorney, Agent, or Firm*—Oblon, Fisher, Spivak, McClelland & Maier

[57] ABSTRACT

A process for producing an ammonium p-styrenesulfonate or polymer thereof which comprises
   reacting an alkali metal p-styrenesulfonate or a polymer thereof with an inorganic ammonium salt in a medium of a hydrophilic alcohol, or a mixture of a hydrophilic organic solvent and water.

8 Claims, No Drawings

PROCESS FOR PRODUCING AMMONIUM AROMATIC SULFONATE

BACKGROUND OF THE INVENTION

1. Field of the Invention

The present invention relates to a process for producing an ammonium aromatic sulfonate, especially ammonium styrenesulfonate or a polymer thereof.

2. Description of the Prior Art

It is known that alkali metal salts of p-styrenesulfonate can be industrially produced by the reaction of p-β-haloethylbenzenesulfonic acid with an alkali metal hydroxide, i.e.,

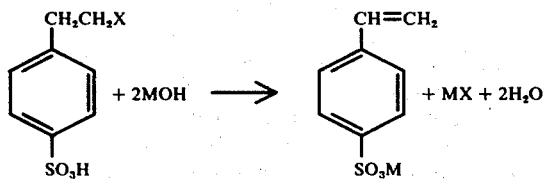

wherein X represents Cl or Br and M represents an alkali metal. When such an alkali metal salt of p-styrenesulfonate is polymerized by radical polymerization, units having molecular weights corresponding to both oligomers and polymers are obtained.

It is also known to the present authors that ammonium p-styrenesulfonate or a polymer thereof can be produced from alkali metal p-styrenesulfonate or a polymer thereof by using an ion exchange resin. However, the process has many attendant disadvantages: a large size apparatus is required in the industrial process low concentrations are required for the operation; the ion exchange rate is low; troublesome absorption phenomena can be caused and the recovery of the ion exchange resin is complicated. Consequently, it would be most desirable to have a process for producing the corresponding ammonium salt of an alkali metal p-styrenesulfonate or a polymer thereof which is highly useful on an industrial scale.

SUMMARY OF THE INVENTION

Accordingly, it is an object of this invention to provide a process for producing an ammonium p-styrenesulfonate or a polymer thereof from the corresponding alkali metal p-styrenesulfonate or a polymer thereof in high purity by a process which is highly suitable for industrial application. This and other objects of this invention as will hereinafter be made clear in the ensuing discussion have been attained by providing a process for producing ammonium p-styrenesulfonate or a polymer thereof which comprises reacting by double decomposition an alkali metal p-styrenesulfonate or a polymer thereof with an organic ammonium salt in a medium which is an alcohol or a mixture of a hydrophilic organic solvent and water.

DETAILED DESCRIPTION OF THE PREFERRED EMBODIMENTS

In either of the solvents mentioned above the solubility of the ammonium p-styrenesulfonate or polymer thereof is remarkably higher than those of the other inorganic salts which are present. This includes the by-products of the reaction, i.e., inorganic salts such as alkali metal sulfates, alkali metal phosphates, alkali metal carbonates, alkali metal chlorides. These solubilities are all very low in contrast. The equilibrium reactions (1), (2), and (3) below are all shifted to the right because of this fact.

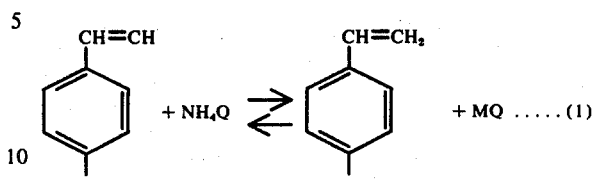

wherein Q is, for example, Cl and M represents an alkali metal;

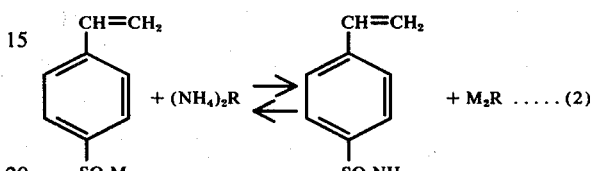

wherein R is, for example, $SO_4$ or $CO_3$; and

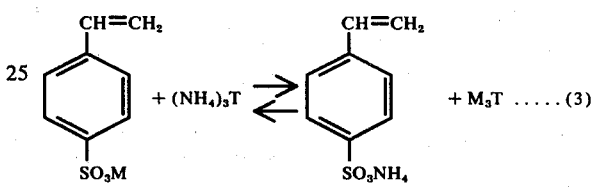

wherein T is, for example $PO_4$. More surprisingly, it has been found that even though a large excess of the inorganic ammonium salt is employed as a reactant in the medium of the equilibrium reaction (1), (2) or (3), only a quite minimal amount of the inorganic ammonium salt contaminates the product in the liquid phase. Most of the excess portion of the inorganic ammonium salt remains undissolved. In other words, the ammonium p-styrenesulfonate or its polymer is highly dissolved in the medium, i.e., the alcohol or mixture of a hydrophilic organic solvent and water, compared with the inorganic ammonium salt with which it shares a common ion. This common ion effect is a key feature of this invention.

Suitable alcohols for use as the medium in this invention include hydrophilic alcohols such as methanol, ethanol, propanol, and the like. Suitable hydrophilic organic solvents include said hydrophilic alcohols, oxygen-containing polar solvents such as acetone, dioxane, tetrahydrofuran, and the like. When a hydrophilic alcohol is used, no other solvents are required. When a mixture of the hydrophilic alcohol and water is used, the polarity of the medium becomes quite high. Consequently, the speed of dissolution of the raw materials is high, thereby shortening the time of operation. However, when the oxygen-containing polar solvents such as acetone, dioxane, tetrahydrofuran (non-alcohol type medium) are used alone, the product compound is not disclosed. Accordingly, it cannot be used by itself, and it is indispensable to employ a mixture of the hydrophilic organic solvent and water. The ratio of the amount of hydrophilic organic solvent to that of water should be preferably higher than 1.0. When the ratio of solvent/water is less than 1.0, the inorganic ammonium salt is also dissolved because of the presence of the water. It is especially preferable to use methanol, ethanol and propanol which contain 10–30 wt. % of water. Accordingly, the purity of the product is decreased.

When the non-alcohol type solvent is used, the ratio of solvent/water should be preferably lower than 10.0.

The amount of alkali metal p-styrenesulfonate or its polymer to be reacted should be lower than 40 parts, preferably 2-20 parts relative to 100 parts of the medium. When the content is higher than 40 parts, the slurry of the alkali metal p-styrenesulfonate or polymer thereof in the medium becomes difficult to handle. Suitable inorganic ammonium salts include ammonium hydrogen sulfate, ammonium sulfate, ammonium bicarbonate, ammonium carbonate, ammonium monohydrogen phosphate, ammonium dihydrogen phosphate, ammonium phosphate, ammonium chloride and the like. An excess amount of the inorganic ammonium salt equal to 1-3 times the equivalent amount is sufficient. Acceptable reaction temperatures can be about 0° C if a quite long operation is acceptable. However, speedy operation is attained at higher temperature, especially at about the boiling point of the medium.

As mentioned above, ammonium p-styrenesulfonate polymer can be produced by reacting an alkali metal p-styrenesulfonate polymer with the inorganic ammonium salt. However, it also can be produced by polymerizing in its reaction mixture the ammonium p-styrenesulfonate which has been prepared by the process of this invention.

Suitable alkali metal p-styrenesulfonate polymers used for the process of the invention include those having a molecular weight in the range of from oligomer weights to about $2 \times 10^6$. When the weight is higher, the product of ammonium p-styrenesulfonate polymer is difficult to dissolve in the medium. Therefore, the reaction is difficult to perform and/or the reaction mixture becomes too viscous for filtration.

Having generally described the invention, a more complete understanding can be obtained by reference to certain specific examples, which are included for purposes of illustration only and are not intended to be limiting unless otherwise specified. In the examples, the term "part" means "part by weight".

EXAMPLE 1

In 100 parts of methanol, 5 parts of sodium p-styrenesulfonate and 5 parts of ammmonium sulfate were charged. The mixture was stirred at 65° C for 3 hours. After cooling to 30° C, the reaction mixture was filtered. The filtrate was condensed and dried to obtain 4.8 parts of ammonium p-styrenesulfonate. Analysis showed that only 0.13 wt. % of Na and 0.01 wt. % $SO_4$ were included in the product.

EXAMPLE 2

In 100 parts of methanol containing 20 wt. % of water, 10 parts of sodium p-sytrenesulfonate polymer (average molecular weight of 365,000) and 10 parts of ammonium sulfate were charged. The mixture was stirred at 20° C for 3 hours. The reaction mixture was then filtered and the filtrate was condensed and dried to obtain 9.7 parts of ammonium p-styrenesulfonate. Analysis showed that only 0.19 wt. % of Na and 0.01 wt. % of $SO_4$ were included in the product.

EXAMPLE 3

In 100 parts of methanol containing 30 wt. % of water, 20 parts of sodium p-styrenesulfonate and 20 parts of ammonium sulfate were charged. The mixture was stirred at 65° C for 30 minutes. After cooling to 30° C, the reaction mixture was filtered and the filtrate was condensed and dried to obtain 18.7 parts of ammonium p-styrenesulfonate. Analysis showed that only 0.14 wt. % of Na and 0.01 wt. % of $SO_4$ were included in the product.

EXAMPLE 4

In 100 parts of n-propanol containing 30 wt. % of water, 10 parts of potassium p-styrenesulfonate and 7.5 parts of ammonium chloride were charged. The mixture was stirred at 20° C for 3 hours. The reaction mixture was filtered and the filtrate was condensed and dried to obtain 8.9 parts of ammmonium p-styrenesulfonate. Analysis showed that only 0.08 wt. % of K and 0.91 wt. % of Cl were included in the product.

EXAMPLE 5

In 100 parts of acetone containing 40 wt. % of water, 10 parts of potassium p-styrenesulfonate and 10 parts of ammonium sulfate were charged. The mixture was stirred at 60° C for 30 minutes. After cooling to 30° C, the reaction was filtered and the filtrate was condensed and dried to obtain 9.0 parts of ammonium p-styrenesulfonate. Analysis showed that only 0.15 wt. % of K and 0.01 of $SO_4$ were included in the product.

EXAMPLE 6

The process of Example 1 was repeated except using 100% ethanol instead of methanol. Similar results were found.

EXAMPLE 7

The process of Example 5 was repeated except using dioxane or tetrahydrofuran instead of acetone. Similar results were found.

EXAMPLE 8

The process of Example 1 was repeated except using ammonium hydrogen sulfate, ammonium bicarbonate, ammonium carbonate, ammonium monohydrogen phosphate, ammonium dihydrogen phosphate or ammonium phosphate instead of ammonium sulfate. Similar results were found.

REFERENCE EXAMPLE

Strongly acidic cation exchange resin (ammonium type) Amberlite IR-120 B (manufactured by Rohm & Hass Co.) and water were filled into a column having an inner diameter of 5 cm and a height of 40 cm. An aqueous solution of 2.5 wt. % of sodium p-styrenesulfonate polymer (average molecular weight of 365,000) was treated by passing it through the column at a rate of 2 cc/min. The solid concentration, Na content, and $NH_4$ content of each fraction of the eluate were analyzed. Conversions were about 70%, as shown in the Table.

TABLE

| Fraction No. (order of elution) | 1 | 2 | 3 | 4 | 5 |
|---|---|---|---|---|---|
| Weight of fraction (g) | 540 | 560 | 520 | 610 | 520 |
| Solid concentration | 1.27 | 1.86 | 2.32 | 2.41 | 2.45 |
| $NH_4$ content (wt.%) | 0.092 | 0.14 | 0.18 | 0.19 | 0.18 |
| Na content (wt.%) | 0.039 | 0.060 | 0.086 | 0.093 | 0.10 |
| Conversion (%) | 75.1 | 74.9 | 72.8 | 72.3 | 69.7 |

The process of the Reference Example was also repeated using potassium p-styrenesulfonate, sodium p-styrenesulfonate or potassium p-styrenesulfonate polymer (average molecular weight of 430,000) instead of the compound above. The conversion was about 70% in each case.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for producing an ammonium p-styrenesulfonate or polymer thereof which comprises:

reacting an alkali metal p-styrenesulfonate or a polymer thereof with an inorganic ammonium salt, in a medium of a hydrophilic alcohol, or a mixture of a hydrophilic organic solvent and water, wherein when said medium is a mixture of a hydrophilic organic solvent and water, the weight ratio of the amount of said solvent to the amount of water is from 1.0 to 10.

2. The process of claim 1, wherein said medium is a hydrophilic alcohol.

3. The process of claim 1, wherein said hydrophilic organic solvent is an oxygen containing hydrophilic solvent.

4. The process of claim 1, wherein less than 40 wt. parts of said alkali metal p-styrenesulfonate or a polymer thereof is admixed with 100 wt. parts of said medium.

5. The process of claim 1, wherein said alkali metal p-styrenesulfonate polymer has molecular weight in the range of the weight of its dimer to $2 \times 10^6$.

6. The process of claim 1, wherein said inorganic ammonium salt is a chloride, bisulfate, sulfate, bicarbonate, carbonate, monohydrogen phosphate, dihydrogen phosphate or phosphate.

7. The process of claim 1, wherein the resulting ammonium p-styrenesulfonate is polymerized in the reaction mixture, so as to form ammonium p-styrenesulfonate polymer by free radical polymerization.

8. The process of claim 1, wherein said medium is methanol, ethanol, propanol or a mixture thereof with water wherein the ratio of said alcohol to the water is higher than 1.0.

* * * * *